United States Patent [19]

Wolf et al.

[11] 4,409,245

[45] Oct. 11, 1983

[54] PROTECTION OF MICROORGANISMS AGAINST BACTERIOPHAGE VIRUS ATTACKS

[75] Inventors: Erich Wolf, Overath; Andreas Lembke, Eutin-Sielbeck; Rolf Deininger, Cologne, all of Fed. Rep. of Germany

[73] Assignee: Chimicasa GmbH, Chur, Switzerland

[21] Appl. No.: 306,409

[22] Filed: Sep. 28, 1981

Related U.S. Application Data

[63] Continuation-in-part of Ser. No. 5,761, Jan. 23, 1979, abandoned.

[30] Foreign Application Priority Data

Jan. 27, 1978 [LU] Luxembourg ............................ 78955
Jan. 2, 1979 [LU] Luxembourg ............................ 80748

[51] Int. Cl.$^3$ .................... A23C 9/12; A23C 9/123; A23C 9/13; C12N 1/04
[52] U.S. Cl. .......................................... 426/9; 426/34; 426/43; 435/260; 435/800
[58] Field of Search .................... 426/9, 11, 34, 36, 43, 426/321, 334, 335; 435/260, 800

[56] References Cited

U.S. PATENT DOCUMENTS 2,964,406 12/1960 Strandskov et al. .................. 426/9
3,022,176 2/1962 Lawrence et al. ...................... 426/9
3,899,594 8/1975 Nickerson et al. ...................... 426/9

OTHER PUBLICATIONS

Uzdennikov, B. N., Effect of Some Terpenes on Bacteria Fungi and Protozoa, Chem. Abstr., vol. 78: 53205n, 1973 (p. 86).
Akimov, et al., Antimicrobial Activity of Terpenes from Juniperus Sabina L., Chem. Abstr., vol. 86: 165837s, 1977 (p. 101).
Uzdennikov, B. N., Biological Activity of Terpenes, Their Mixtures, and Common Pine Turpentine, Chem. Abstr., vol. 77: 160481a, 1972 (p. 58).
De Clerck, J., A Textbook of Brewing, vol. One, Chapman and Hall, London, 1957 (pp. 58–62).

*Primary Examiner*—David M. Naff
*Attorney, Agent, or Firm*—Kontler, Grimes & Battersby

[57] ABSTRACT

Living cultures of microorganisms used in the preparation of foodstuffs by microbiological processing are protected against attack by bacteriophage viruses by the addition thereto of terpene. The terpene is added in an amount which is effective to obtain viricidal activity but ineffective to cause toxic effects on the microorganisms. The terpene is one obtainable from aromatic plants by steam distillation. Terpenes or mixtures of terpenes which have proved suitable are those obtained from black pepper oil, cinnamon flower oil, cardamon oil, linallyl acetate, cinnamic aldehyde, safrol, carvon and cis/ trans citral, used individually or mixed together. They may added dissolved in a carrier such as 1,2-propanediol. The terpenes demonstrate a viricidal activity in a concentration which is one or more powers of ten lower than the concentration at which the terpenes have toxic effects on the microorganisms.

4 Claims, No Drawings

PROTECTION OF MICROORGANISMS AGAINST BACTERIOPHAGE VIRUS ATTACKS

This application is a continuation-in-part of application Ser. No. 005,761, filed Jan. 23, 1979, now abandoned.

BACKGROUND OF THE INVENTION

This invention relates to the preparation of foodstuffs using microbiological processing with living cultures of microorganisms and particularly to a method and composition for protecting such cultures against attack by bacteriophage viruses.

In processes for preparing food using micro-organisms, a living culture of the microorganisms, capable of multiplying, is inoculated into the food which is to be prepared and living conditions appropriate to maintaining the desired activity of the microorganisms are created and maintained, for the duration of the desired activity, by adding nutrients and/or by adjusting the temperature, humidity and/or pH value.

Much industrial food preparation, such as for example fermentation and caseation, is carried out using microorganisms, such as bacteria, yeasts, fungi or algae. These microorganisms are subject to attack by bacteriophage viruses both in the cultures in which they are kept and also during their action on the foods. Such attacks can disrupt the conversion processes being carried out using the microorganisms.

Cultures used in the production of foodstuffs are attacked by bacteriophages and become spoiled unless one exercises great care. A culture must be protected from such attack both during storage in its inactive stages of growth as well as during its active stages of growth, that is, when it multiplies in use in processing. Spoiled cultures cannot be used to effect the desired microbiological process in the foodstuffs. Instead, other, undesirable, microorganisms, which penetrate into the foodstuffs from the outside or which are already contained in the foodstuffs, become effective and multiply accordingly. The effect of such other microorganisms is, as a rule, to cause the foodstuffs to spoil. Since microbiological processing of foodstuffs presupposes the use of special, selected pure cultures, attack and destruction by viruses such as phages is undersirable.

SUMMARY OF THE INVENTION

An object of this invention is the minimization and/or prevention of such phage attacks against microorganisms used in food preparation.

The object is achieved, according to this invention, by adding terpene obtainable from aromatic plants by steam distillation to the foods in a quantity of 1 to 1000 mg (milligrams) of terpene per 10 kg (kilograms) of food, then mixing them together and causing them to be acted on.

These terpenes demonstrate a viricidal activity, that is, a damaging effect on viruses, in a concentration which is one or more powers of ten lower than the concentration at which these terpenes have toxic effects on living cells. This wide range permits a degree of margin, which is advantageous from the dosage point of view, within which the desired viricidal activity can be achieved without any danger of also damaging the microorganisms.

Since these terpenes can be obtained from aromatic plants which have been used for feeding animals and humans for many years and have proved harmless in the doses in question, it is ensured that the quantities of terpenes to be used according to the invention will not have any harmful effects when the food thus treated is consumed.

Since the desired viricidal effect can be obtained with relatively small added amounts of the terpenes, the flavor of the foods will not be affected by the terpenes.

After inoculation into the foodstuff, the microorganisms multiply and the terpene needed to protect this total number of microorganisms can be added to the food beforehand, or alternatively, the terpene can be added in successive portions over a period of time in accordance with the growth of the population of microorganisms. When protecting a microorganism culture in its inactive state of growth, during storage, the amount of terpene needed to protect the culture can simply be added at one time.

Terpenes or mixtures of terpenes which have proved suitable are those obtained from black pepper oil, cinnamon flower oil, cardamon oil, linallyl acetate, cinnamic aldehyde, safrol, carvon and cis/trans citral, used individually or mixed together. They may be advantageously added dissolved in a carrier such as 1,2-propanediol.

The terpenes used can be obtained from aromatic plants by steam distillation as follows: black pepper oil from the peppercorns of Piper nigrum; cinnamon flower oil from the flowers of Cinnamonum Cassia; cardamon oil from the seeds of Elettaria Cardamomum; linallyl acetate from the flowers of Lavandula; cinnamic aldehyde from the bark of Cinnamonum ceylanicum; safrol from the root of Sassafras; carvon from the fruit of Carum carvi, and cis/trans citral from the leaves of Cymbopogon citratus.

DESCRIPTION OF THE PREFERRED EMBODIMENTS

The results obtained and the advantages and utility of the invention are demonstrated by comparison tests in the following examples.

Comparison tests were made using living cell cultures and viruses, as is customary in microbiological testing, from which those skilled in the art can predict the results that will be obtained with other microorganisms, of the type used in the preparation of food, and other viruses.

Cell cultures were cultivated in various culture vessels under optimal culture conditions from permanent strains of the types "Girardi Heart" (GH), "Flow 12000" (FL), "Intestine 407" (IN) and "Vero Kidney" (VE), so that a layer of cell culture containing about 0.25 mg of cell substance formed on the bottom of the vessels.

A suspension of virus particles of the Adeno Type 6 virus was also added.

For the total of eight terpenes listed in Table I, twenty cell cultures of each type of cell were prepared. The twenty cell cultures of each type of cell were treated with differing amounts of the relevant terpene in the following manner.

The first two cell cultures were given $10^5$ mg of terpene per 10 kg of cell substance. The next two cell cultures were given $10^4$ mg of terpene based on 10 kg of cell substance. The next two cell cultures were given $10^3$ mg of terpene based on 10 kg of cell substance and so on to the last two of these twenty cell cultures, which were given 0.1 mg of terpene per 10 kg of cell substance. Thus, in each case, two similar cell cultures were treated with the same amount of the same terpene. For control purposes, one of these two identical cell cultures was left as it was, while the other was inoculated with $5 \times 10^6$ virus particles per 0.25 mg of cell substance, in addition to the virus suspension used. The same procedure was also followed with the other cell cultures and terpenes.

The cell cultures thus treated were left to stand and observed after four days and six days. This observation was carried out by microscopic investigation of the cell culture for cell damage. The damage observed was divided into four stages, as follows:

| | | |
|---|---|---|
| Stage 0 | means | no damage |
| Stage 1 | means | slackened growth of the cell formations |
| Stage 2 | means | the cells become spherical and detach themselves from the bottom |
| Stage 3 | means | the cell structures are substantially or totally destroyed. |

It was found that the inoculated cell cultures which were protected with a very small amount of terpene reached state 3 or 2, as the viruses had damaged the cells. The inoculated cell cultures containing a very large amount of terpene also reached stage 3 or 2, as the cells were damaged by the excessive terpene. However, the inoculated cell cultures containing only a moderate amount of terpene were at stage 0, that is, undamaged. Thus, the moderate amount of terpene damaged the viruses sufficiently and protected the cells from viral attack, without the cells being damaged directly by the terpene. The terpene concentrations with which stage 0 and, in some isolated cases, stage 1 were observed in the inoculated cell cultures after four and six days result in sufficient damage to the viruses without damaging the cells, and are set forth in Table I.

The first column of Table I gives the terpene used, the second column gives the treated cell strain, abbreviated as hereinbefore, and the third column gives the amount of terpene used in mg, based on 10 kg of treated cell substance, for the range of concentrations in which no appreciable cell damage (that is, stage 0) was observed. This range is the "effective" viricidal range which in each case extends over several powers of ten. Thus, for all the terpenes listed in Table I, the desired viricidal activity occurs at a concentration which is several powers of ten lower than the lowest concentration at which cell damage was observed, that is, at which the microorganisms to be protected could be damaged.

TABLE I

| Terpene | Treated Cell Substance | Range of Viricidal Concentration |
|---|---|---|
| black pepper oil | GH | $10^3$ to 0.1 |
| (Oleum *Piperis nigri*) | FL | 100 to 0.1 |
| | IN | 100 to 1 |
| | VE | 100 to 0.1 |
| Cinnamon flower oil | GH | $10^3$ to 0.1 |
| (Oleum *Cassiae flores*) | FL | $10^3$ to 0.1 |
| | IN | 100 to 0.1 |
| | VE | 100 to 0.1 |
| Cardamom oil | GH | 100 to 1 |

TABLE I-continued

| Terpene | Treated Cell Substance | Range of Viricidal Concentration |
|---|---|---|
| (Oleum Cardamomi) | FL | 100 to 1 |
| | IN | 100 to 1 |
| | VE | 100 to 10 |
| Linallyl acetate | GH | 100 to 0.1 |
| | FL | 100 to 1 |
| | IN | 100 to 1 |
| | VE | 100 to 1 |
| cinnamic aldehyde | GH | 100 to 1 |
| | FL | 100 to 1 |
| | IN | 100 to 1 |
| | VE | 100 to 1 |
| safrol | GH | 100 to 1 |
| | FL | 100 to 1 |
| | IN | 100 to 10 |
| | VE | 100 to 1 |
| carvon | GH | 100 to 1 |
| | FL | 100 to 1 |
| | IN | 100 to 1 |
| | VE | 100 to 1 |
| cis/trans citral | GH | 10 to 1 |
| | FL | 10 to 1 |
| | IN | 100 to 1 |
| | VE | 100 to 1 |

EXAMPLE 1

In the preparation of yoghurt, 100 l of cows' milk were sterilized and then adjusted to 40° C. Then, 500 mg of black pepper oil were added to the milk, thoroughly mixed by stirring, and the milk inoculated with a pure culture of the lactic acid bacteria Lactobacillus bulgaricus. The mixture was left to stand for 12 hours at 40° C., and observed to be protected from external effects such as would result from attack by phages, until the yoghurt was formed.

The examples given are open to variation by using, instead of the black pepper oil, the same amount of another terpene from Table I or a mixture of several of these terpenes. The amount of terpene added can also be modified within the range described provided that an amount effective to obtain the viricidal activity but ineffective to result in toxic effects on the microorganism culture, is used. In all these cases, a viricidal effect is obtained without any effect on the flavor or other desirable qualities.

EXAMPLE 2

Black pepper oil is obtained from black pepper by steam distillation. The black pepper oil is dissolved in 1,2-propanediol in a weight ratio of 1:50. The solution is sterilized in an autoclave for 50 minutes at 121° C. The terpene composition thus obtained is added to the food which is to be prepared using microorganisms, in a weight ratio of 50 mg to 5.0 g of terpene composition to 10 kg of food, which corresponds to 1 to 100 mg of terpene to 10 kg of food. Instead of using black pepper oil, the same amount of another terpene from Table I or a mixture of several terpenes may be effectively employed. Also, the weight ratio of terpene to 1,2-propanediol can be altered within the range from 1:10 to 1:1000. However, when adding the terpene composition to the food, the amount added must be such as to obtain the desired concentration of 1 to 100 mg of terpene per 10 kg of food. The terpene composition is especially suitable for adding the terpene to the food but can also be used in conjunction with Example 1.

The foregoing results demonstrate that cultures of microorganisms used for the preparation of foodstuffs by microbiological processing can be protected against attack by bacteriophage viruses, surprisingly without harmful effects on the microorganisms themselves, by adding thereto proper viricidal dosages of terpene according to this invention. This was further confirmed by comparison tests described in the following Examples 3 to 10.

The comparison tests of Examples 3 to 10 were carried out in a manner similar to those on which the results set forth in Table I are based with the sole exception that, instead of the virus Adeno type 6, the virus phage 034 was used and instead of cells GH, FL, IN and VE, use was made of the following microorganisms: streptococcus lactis (SL), streptococcus cremoris (SC), and streptococcus diacetylicatis (SD).

Phage 034 can be morphologically described as being $89 \pm 2$ nm long with a $65 \times 44$ nm head and existing collar and a short, $24 \times 10$ nm, tail. It can be obtained from the Institut fur Virusforschung und Experimentelle Medizin, D-2420 Eutine Sielbeck, West Germany.

EXAMPLE 3

A culture of streptococcus lactis (SL) was permeated with 80 mg black pepper oil per 10 kg of culture substance, mixed and thereupon vaccinated with $2 \times 10^7$ phage parts per mg culture substance of the phage 034 and left standing for 2 hours. For the preparation of sour milk, 100 l cow's milk were sterilized and then maintained at 28° C. In the next step, 100 g of the culture which had been permeated with the black pepper oil were added to the milk and thoroughly mixed by stirring. The mixture remained standing at 28° C. for 8 hours until the milk curdled and assumed the consistency which is desired for consumption. No harmful effects of the phage were observed.

EXAMPLE 4

The same procedure as in Examples 3 was followed with the sole difference that the culture was streptococcus diacetylactis (SD) which was permeated with 100 mg of cinnamon aldehyde per 10 kg of culture substance. Again, no harmful effects were observed.

EXAMPLE 5

A culture of streptococcus cremoris (SC) was permeated with 200 mg of black pepper oil per 10 kg culture substance, mixed and thereupon vaccinated with $2 \times 10^7$ phage parts per mg of culture substance and left standing for 2 hours. 300 l butter milk for sour cream were sterilized and maintained at 18° C. This was thereupon mixed with 9 kg of the culture substance which had been permeated by the black pepper oil, and the resulting mixture was left standing for 8 hours until curdling so as to assume the consistency which is desired for consumption. No harmful effects of the phage were observed.

EXAMPLE 6

The same procedure as in Example 5 was followed with the sole difference that, instead of black pepper oil, use was made of cinnamic aldehyde in an amount of of 100 mg per 10 kg of culture substance.

EXAMPLES 7-10

The procedures of Examples 3-6 were repeated but the microorganism cultures were not protected, that is, there was no admixture of the terpenes of black pepper oil or cinnamic aldehyde. It was observed that the cultures were destroyed by the phages. There was no development of sour milk or sour cream and a foul smell developed after approximately 14 hours. The product was spoiled and became useless for the feeding of humans.

The results of Examples 3-10 and similar experiments using other terpenes are set forth in Table II and confirm the beneficial effect which was predictable from the results set forth in Table I, that is, that terpenes develop a phage virus inhibiting action when applied in concentrations which do not entail damage to microorganisms which are affected by phages. Thus, by resorting to proper dosages of terpenes, cultures of microorganisms can be protected from an attack of phages or can be protected in the event of an attack by phages.

TABLE II

| Terpene | Treated Cell Microorganism | Range of Viricidal Concentration |
|---|---|---|
| Black pepper oil | SL | $10^3$ to 10 |
| (Oleum *Piperis nigri*) | SC | $10^3$ to 100 |
| | SD | $10^3$ to 10 |
| Cinnamon flower oil | SL | $10^3$ to 10 |
| (Oleum *Cassiae flores*) | SC | $10^3$ |
| | SD | $10^3$ to 100 |
| Cardamom oil | SL | $10^3$ to 100 |
| | SC | 100 |
| | SD | 100 |
| Linallyl acetate | SL | 100 to 10 |
| | SC | 100 |
| | SD | 100 |
| Cinnamic aldehyde | SL | $10^3$ to 100 |
| | SC | 100 |
| | SD | 100 |
| Safrol | SL | $10^3$ to 100 |
| | SC | 100 |
| | SD | 100 |
| Carvon | SL | $10^3$ to 100 |
| | SC | 100 |
| | SD | $10^3$ to 100 |
| cis/trans citral | SL | 100 to 10 |
| | SC | 10 |
| | SD | 100 to 10 |

As with Table I, the third column of Table II gives the amount of terpene used in mg, based on 10 kg of treated microorganism culture substance, for the range of concentrations in which no damage from the phage was observed. This range is the "effective" viricidal range which in each case extends over several powers of ten. Thus, for all the terpenes listed, the desired viricidal activity occurs, as for those in Table I, at a concentration which is several powers of ten lower than the lowest concentration at which damage was observed.

I claim:

1. A method for protecting a living culture of microorganisms selected from the group consisting of streptococcus lactis, streptococcus cremeris and streptococcus diacetylicatis from attack by phage viruses comprising adding to the microorganism culture a terpene capable of demonstrating a viricidal activity against phage viruses in an amount effective to obtain such viricidal activity but ineffective to cause toxic effect in the microorganisms, wherein said terpene is selected from the group consisting of black pepper oil, cinnamon flower oil, cardamom oil, linallyl acetate, cinnamic adehyde, safrol, carvon, cis/trans citral and combinations thereof.

2. A method for protecting a living culture of microorganisms as claimed in claim 1 wherein the terpene is added to the microorganism culture in a maximum amount which provides a concentration which is one or more powers of ten lower than the concentration at which toxic effects on the microorganisms are observed.

3. The method for protecting a living culture of microorganisms as claimed in claim 1 wherein the terpene is one obtainable by steam distillation from aromatic plants.

4. In a process for the preparation of food including the steps of inoculating the food with a living culture of a microorganism and maintaining the inoculated food under conditions such that the microorganism becomes active to participate in microbiological processing of the food the improvement comprising selecting as the living culture of microorganisms one selected from the group consisting of the lactic acid bacteria Lactobacillus bulgaricus, streptococcus lactis, streptococcus cremoris and streptococcus diacetylicatis, protecting the microorganisms from the harmful external effects of phage viruses by incorporating in the food and microorganism culture mixture a compound selected from the group consisting of black pepper oil, cinnamon flower oil, cardamom oil, linallyl acetate, cinnamic aldehyde, safrol, carvon, cis/trans citral and combinations thereof in an amount effective to protect the microorganism culture from the harmful external effects without adversely affecting the microorganism culture or the suitability of the food produced for human consumption.

* * * * *